United States Patent [19]
Hadjicostis et al.

[11] Patent Number: 5,924,993
[45] Date of Patent: Jul. 20, 1999

[54] INTRAVASCULAR ULTRASOUND MIXED SIGNAL MULTIPLEXER/PRE-AMPLIFIER ASIC

[75] Inventors: Andreas Hadjicostis, Lone Tree, Colo.; Brian B. North, Los Gatos, Calif.; Bart A. Holmberg, Bellevue, Wash.

[73] Assignee: Advanced Coronary Intervention, Inc., Englewood, Colo.

[21] Appl. No.: 08/950,900

[22] Filed: Oct. 15, 1997

[51] Int. Cl.⁶ ........................................... A61B 8/00
[52] U.S. Cl. ............................. 600/462; 600/447
[58] Field of Search ..................... 600/459–471, 600/447; 29/25.35; 310/334, 335, 336; 73/626

[56] References Cited

U.S. PATENT DOCUMENTS

| | | |
|---|---|---|
| D. 347,896 | 6/1994 | Dickinson . |
| 3,938,502 | 2/1976 | Bom . |
| 4,505,156 | 3/1985 | Questo . |
| 4,543,960 | 10/1985 | Harui . |
| 4,841,977 | 6/1989 | Griffith . |
| 4,917,097 | 4/1990 | Proudian . |
| 5,027,659 | 7/1991 | Bele . |
| 5,109,861 | 5/1992 | Walinsky . |
| 5,186,177 | 2/1993 | O'Donnell . |
| 5,226,847 | 7/1993 | Thomas, III . |
| 5,257,629 | 11/1993 | Kitney . |
| 5,273,045 | 12/1993 | Chihara . |
| 5,402,793 | 4/1995 | Gruner . |
| 5,453,575 | 9/1995 | O'Donnell et al. ...................... 600/462 |
| 5,456,259 | 10/1995 | Barlow . |
| 5,465,726 | 11/1995 | Dickinson . |
| 5,509,827 | 4/1996 | Huppenthal . |
| 5,522,393 | 6/1996 | Phillips et al. ........................... 600/455 |
| 5,590,659 | 1/1997 | Hamilton . |
| 5,601,082 | 2/1997 | Barlow . |
| 5,630,421 | 5/1997 | Barlow . |
| 5,817,024 | 10/1998 | Ogle et al. ............................... 600/447 |

FOREIGN PATENT DOCUMENTS 0 671 221 A2  9/1995  European Pat. Off. .

OTHER PUBLICATIONS

A. Gachagan, 1996 IEEE Ultrasonics Symposium, Construction and Evaluation of a New Generation of Flexible Ultrasonic Transducers, 1996.

Loriann L. Ries, 1996 IEEE Ultrasonics Symposium, Phase Aberration Correction in Two Dimensions With An Integrated Deformable Actuator/Transducer, 1996.

Charles D. Emery, 1996 IEEE Ultrasonics Symposium, Signal To Noise Ratio of Hybrid Multilayer/Single Layer 2–D Arrays, 1996.

Richard E. Davidsen, 1996 IEEE Ultrasonics Symposium, A Multiplexed Two–Dimensional Array For Real Time Volumetric and B–Mode Imaging, 1996.

Stephen W. Smith, 1995 IEEE Ultrasonics Symposium, Update On 2–D Array Transducers For Medical Ultrasound, 1995.

Loriann L. Ries, 1995 IEEE Ultrasonics Symposium, Phase Aberration Correction in Two Dimensions Using A Deformable Array Transducer, 1995.

(List continued on next page.)

*Primary Examiner*—Francis J. Jaworski
*Assistant Examiner*—Ali M. Imam
*Attorney, Agent, or Firm*—Gibson, Dunn & Crutcher LLP

[57] ABSTRACT

An ultrasound mixed signal multiplexer/pre-amplifier application specific integrated circuit (ASIC) for supplying voltages to a group of elements of an ultrasound array, receiving voltages from the same or another group of elements of the array, and amplifying the received voltages for transmission to external circuitry. The transmit groups and receive groups are shifted to provide accurate visual images with a minimal number of transmit and receive cycles.

12 Claims, 8 Drawing Sheets

OTHER PUBLICATIONS

J.E. Piel, Jr., 1994 Ultrasonics Symposium, MHZ Pediatric Phased Array Transesophageal Endoscope, 1994.

Richard E. Davidsen, 1996 IEEE Ultrasonics Symposium, A Multiplexed Two–Dimensional Array For Real Time Volumetric and B–Mode Imaging, 1996.

Stephen W. Smith, 1995 IEEE Ultrasonics Symposium, Update On 2–D Array Transducers For Medical Ultrasound, 1995.

Loriann L. Ries, 1995 IEEE Ultrasonics Symposium, Phase Aberration Correction in Two Dimensions Using A Deformable Array Transducer, 1995.

A. Gachagan, 1996 IEEE Ultrasonics Symposium, Construction and Evaluation of A New Generation of Flexible Ultrasonic Transducers, 1996.

Loriann L. Ries, 1996 IEEE Ultrasonics Symposium, Phase Aberration Correction In Two Dimensions With An Integrated Deformable Actuator/Transducer, 1996.

Charles D. Emery, 1996 IEEE Ultrasonics Symposium, Signal To Noise Ratio of Hybrid Multilayer/Single Layer 2–D Arrays, 1996.

William C. Black, Jr., 1994 IEEE Journal of Solid–State Circuits, vol. 29, No. 11, CMOS Chip For Invasive Ultrasound Imaging, Nov. 1994.

INTRAVASCULAR ULTRASOUND MIXED SIGNAL MULTIPLEXER/PRE-AMPLIFIER ASIC

FIELD OF THE INVENTION

The present invention relates to the field of electronic mixed signal multiplexers and pre-amplifiers (integrated circuits), and more particularly to those that are capable of insertion into a lumen of a human body for ultrasound medical imaging techniques.

BACKGROUND

Ultrasonic imaging from within the body of a patient has been used for some time, particularly in the treatment of heart disease. While alternative methods of sensing the condition of diseased vasculature exist, such as the injection and monitoring of radiopaque dyes, ultrasound is the most promising technology for accurately viewing the interior of a body in real time and in a non-destructive manner.

Such imaging techniques are particularly useful in connection with an angioplasty device that removes a built-up deposit within a lumen. Successful removal depends upon accurately locating the deposit in relation to the device. It is desirable that the resolution of a visualization technique be at least commensurate with the degree of resolution of the ablation device. The present invention has particular utility with high resolution ablation devices. An example of such a device is described in U.S. Pat. Nos. 5,626,576 and 5,454,809, commonly owned with the present invention. In such a device, radio frequency current is selectively deployed around the circumference of a lumen such as a coronary artery, depending upon the position of the occlusive material. The imaging used with such a device should enable the user to determine the circumferential position of the deposit. In general, prior art ablation techniques have not required the visualization resolution provided by the present invention.

In an in vivo ultrasound imaging system, an array of piezoelectric transducer elements residing on a catheter are introduced into a body. The elements are excited at ultrasound frequencies to transmit acoustical waves, and receive echos as the acoustical waves reflect from the surrounding material. The echos provide electrical signals which are processed to form the ultrasound image.

Previous in vivo ultrasound images have included a number of limitations. The simplest systems use a mechanical scanning system. A flexible drive cable rotates a single element to scan a cross sectional image of a lumen. Problems associated with mechanical systems include jitter, and the limitation of fixed transmit and receive focus restricts clarity and resolution of an image away from the focal point.

Current ultrasound systems utilize sampled phased (PS) arrays, wherein one wire is multiplexed to any one of the elements of an ultrasound array. A first element is individually pulsed, and then the same element receives the echos. A next element is then pulsed and received, and the process is repeated for each array element. A problem with this technique is that cross-product terms are ignored. A cross-product term is where, for example, a first element is pulsed and a second element receives the pulse. This lack of cross-product terms caused grating lobes and increased sidelobe levels. See O'Donnel et al., "Experimental Studies on an Efficient Catheter Array Imaging System" (Ultrasonic Imaging 17, pp. 83–94, 1995). While some modern systems do include cross-product terms (see U.S. Pat. No. 5,590,659 (Hamilton et al., 1997), they are believed to involve a relatively high number of processing steps to do so. This is because the cross products are determined through mathematical reconstructions after transmitting with a single element and receiving with another single element.

Additional problems associated with PS systems are acoustic pressure limitation and ring down artifact. Regarding the acoustic pressure limitation, the PS system cannot receive greater pressure than a single element can provide. Element SNR (signal-to-noise ratio) is typically less than 0 dB. A compensatory technique for such low SNR is averaging multiple independent actuations for each element. While such an averaging technique reduces noise, it can result in noticeable image smearing. The main component of ring down is when the transmit and receive element are the same. When such an element is first switched to receive, it is still "ringing" from transmit. One such PS ultrasound system is described in U.S. Pat. No. 4,917,090 of Proudian et al. In that system a 1×16 multiplexer is provided; that is, a multiplexer selects one transducer element from an array of 16 elements in both transmit and receive modes. To form a useful image from a limited sample, a synthetic aperture focusing technique is used. While that may provide acceptable image quality is some applications, the limited partial sampling is not believed to provide sufficient image quality required for the successful application of advanced ablation techniques such as described above.

It can be appreciated that an in vivo ultrasound visualization system providing improved image quality will allow for more successful treatment of occluded lumens. A key component of such a system is an multiplexer/preamplifier circuit as provided in the present invention. Such a circuit must be able to be physically inserted within a lumen, which imposes significant design constraints. The circuit described herein has particular, although not exclusive, application with a transducer array probe such as described in co-pending application "Ultrasound Transducer Array Probe for Intraluminal Imaging Catheter" filed under atty. docket no. 010848-0017. While the present invention may be described in the context of a coronary artery and atherosclerosis, the application of the invention is not so limited and may be used in the imaging of any lumen within a body, or, conceivably, any other enclosed area.

All documents referred to herein are hereby incorporated by reference to the extent they contain information necessary or helpful to an understanding of the present invention.

SUMMARY

An improved multiplexer pre-amplifier ASIC (referred to as "MUX") for use in an intralumen visualization system is provided.

The MUX delivers voltage to a subset of ultrasound elements in a transmit mode, receives voltages form reflected ultrasound echos in a receive mode, and amplifies these voltages to external circuitry. The MUX selects successively different subsets of ultrasound elements for transmitting and receiving, for each scanline taken. This selection of subsets of ultrasound elements, termed sub-apertures, allows for cross-products to be included without an undue number of transmit and receive cycles.

A primary advantage of the present invention is a faster frame rate (i.e., the time required to acquire an ultrasound image) than known systems. Another primary advantage is better image quality (improved signal to noise ratio (SNR)). Such advantages are achieved in a physical package that is capable of insertion into a lumen of a patient.

These and other features of the invention may be understood with reference to this disclosure and more particularly the drawings and detailed description below.

DETAILED DESCRIPTION

Figure 1:
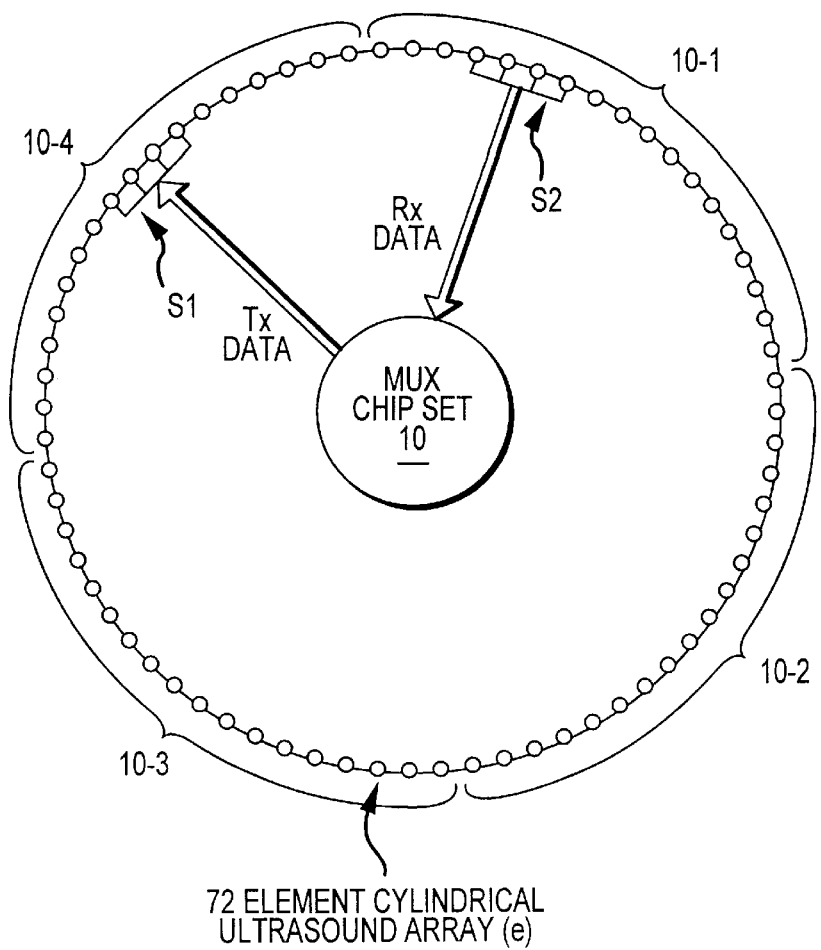
FIG. 1 is a schematic representation of a cylindrical ultrasound array and control elements according to an embodiment of the invention.

The present invention relates to the field of electronic devices and more particularly to a multiplexer pre-amplifier integrated circuit (MUX) for use in an intralumen visualization system. In such a system, a catheter having an ultrasound array is inserted through a lumen of a patient (such as coronary vasculature). The catheter may include means for removing obstructions within the lumen, such as a radio frequency electrosurgical ablation device according to U.S. Pat. No. 5,454,809 of Michael Janssen and commonly owned with the present invention. The ultrasound array allows obstructive material to be precisely located so that the obstruction removal means can be selectively deployed.

The MUX pre-amplifier is a component of an overall ultrasound system that is now described in overview. An array subsystem includes all of the components positioned at a distal end of the catheter. All elements of the array subsystem have a suitably small cross section to fit within such a lumen, such as for example less than about 3.5 French (F) in the case of coronaries. The array subsystem includes the MUX pre-amplifier. Other array subsystem elements include the ultrasound array, an absorbing backing layer for the array, and electrical connector interconnection means such as bundled coaxial cables, electrical connectors, capacitors, and flexible circuit interconnect boards. Only the necessary minimum amount of components are packaged within the distal catheter end because of the extreme space limitations; all other components are packaged external to the catheter.

The external system architecture includes data acquisition boards having analogue and digital signal processing (DSP) capability and control circuit elements that interface with the MUX pre-amplifier. The data acquisition boards communicate through electronic link ports with a central processing unit (CPU) running beamformer software, scan converting and image processing software, and user interface software to control the imaging array and allow the imaging information obtained from the imaging array to be usefully presented. The CPU also provides a convenient platform to support user interface hardware such as a graphic display monitor and a video cassette recorder, a printer, input means such as a keyboard and mouse, and a network connection so that the ultrasound information can be centrally accessed and distributed.

The requirements of the ultrasound imaging system can best be understood in connection with a treatment system such as RF ablation. The ultrasound should provide a 360 degree view since obstructive material may be asymmetrically situated within a lumen.

The system should be capable of providing real time imaging, so that material seen by the ultrasound can be ablated, and the ablation can be monitored and adjusted in conjunction with the imaging.

The present invention provides improved ultrasound imaging by switching multiple parallel channels of transmit and receive acoustic data, and by independently addressing transmit and receive sub-apertures. These features are described below, and it should be appreciated that a considerable challenge was presented in providing these features within the size constraints imposed by the intralumen environment.

Figure 2:
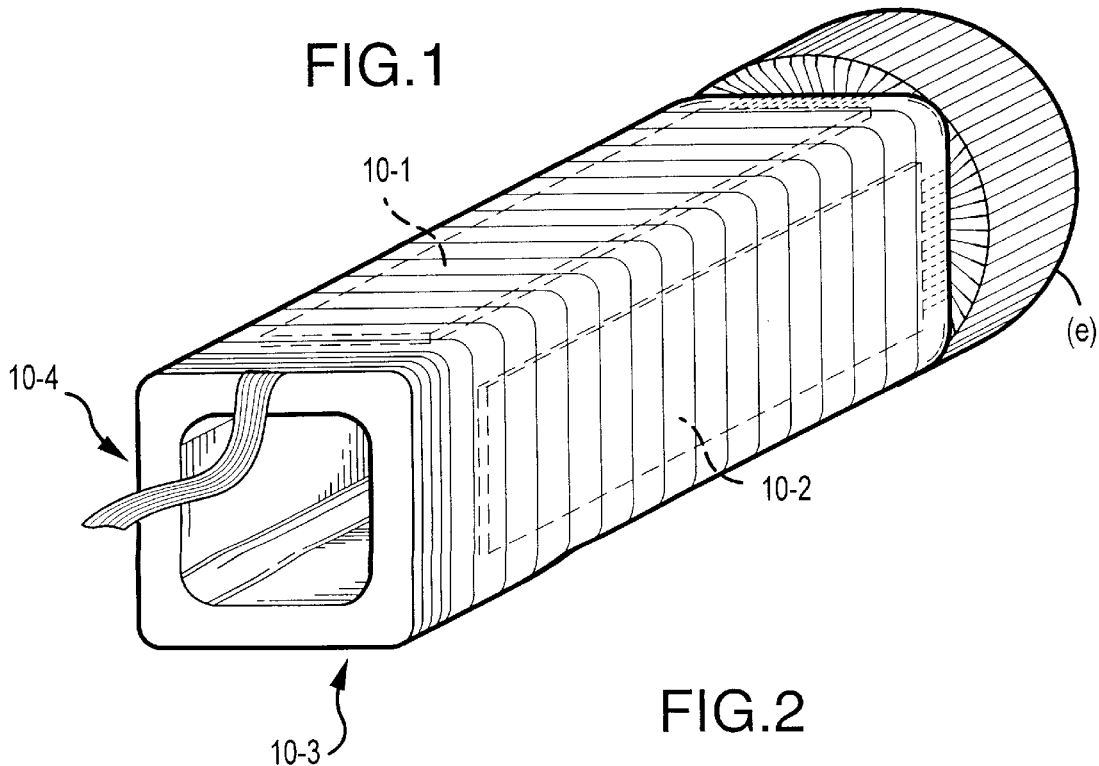
FIG. 2 is a pictorial view of a the cylindrical ultrasound array of FIG. 1 and a group of four multiplexer pre-amplifier integrated circuit (MUXes).

Referring to schematic representation of FIG. 1 and the pictorial representation of FIG. 2, a preferred embodiment of the invention uses a set of four ASIC (application specific integrated circuit) MUX pre-amplifier chips (10) (hereinafter referred to as "MUX (10)" in the singular or "MUXes (10)" in plural). The MUXes (10) are referred to individually, when necessary, as MUX 10-1, 10-2, 10-3, and 10-4. The entire array includes 72 elements, and each MUX (10) controls eighteen adjacent ultrasound elements (e). The elements are in a circle so that the array is cylindrical; however the present invention may be useful for arrays having other configurations. The MUX (10) selects a reduced set of four adjacent elements (e) (or possibly fewer than four) for transmitting and receiving ultrasound signals, the reduced set of elements constituting a sub-aperture. As explained in more detail below, each transmit sub-aperture preferably will be received by that same sub-aperture, and also by other sub-apertures so that cross terms are included. A sample transmit sub-aperture S1 is shown in FIG. 1, as is a sample receive sub-aperture S2. It is a purpose of the MUXes (10) to transmit a pulse to a sub-aperture such as S1, and to receive a pulse from a sub-aperture such as S2. The electronic pulses are converted to and from acoustical pressure by the elements (e), as is well known in the field of ultrasound imaging. Each element (e) is separately connected to an analogue channel C1–C4. The primary complexities are selecting the sub-apertures, and amplifying received signal pulses.

Figure 3:
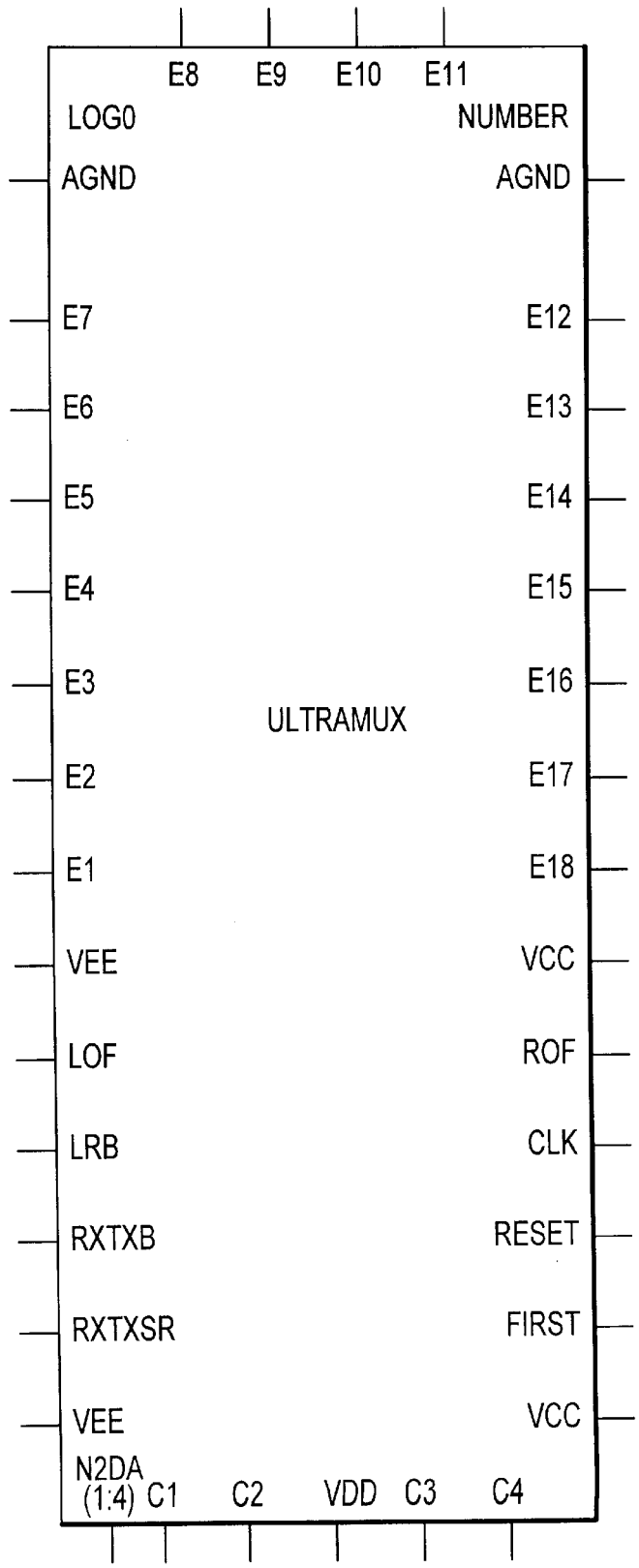
FIG. 3 is an input/output pad layout of the MUX as shown in FIG. 2.

Referring to FIG. 3 and Table 1 below, a pad layout for MUX (10) used in an embodiment of the invention is described. While it should be appreciated that other pad layouts can be used, the pad definitions below further the understanding to the operation of a particular embodiment of the invention. An ASIC embodying the present invention has been constructed having a thickness of 125 micrometers ($\mu$m), width of 600 $\mu$m, and length of 1400 $\mu$m.

TABLE 1

| Pad Layout | |
|---|---|
| E1, E2, ... E18 | bi-directional analogue connections to transducer elements e1–e18 |
| C1, C2, C3, C4 | bi-directional analogue cable connections to the external ultrasound system |
| Agnd | Analogue Ground (0 V) |
| Vdd | Digital positive supply (0 V) |
| Vcc | Analogue positive supply (+4 V) |
| Vee | Negative supply and substrate |

TABLE 1-continued

Pad Layout

| | |
|---|---|
| | connection (−4 V) |
| LOF | Left Overflow (logic bi-directional, Active High) |
| ROF | Right Overflow (logic bi-directional, Active High) |
| RxTxb | Switch between Rx and Tx operating modes (logic input: High = Rx mode, Low = Tx mode) |
| RxTxSR | Switch between Rx and Tx shift registers (SR) (logic input: High = RxSr selected, Low = TxSR selected |
| Reset | Global digital reset (logic input: Active High) |
| First | Master/Slave control signal (logic input: Active High Master; Active Low = Slave) |
| LRB | Left/Right shift control |
| Clk | main clock for shifting left and right (logic input) |

Each MUX (10) has four parallel bi-directional analogue channels (C1, C2, C3, and C4), an analogue channel being a channel that transmits a voltage applied to or received from an array element (e). The parallel analogue channels allow acoustical pressure to be received from each of the four elements (e) comprising a sub-aperture to be received simultaneously after one transmit sequence. Each MUX (10) has a number of power and digital control lines as defined in the Table 1 and described below to control the operation of the analogue channels.

Each analogue channel is either connected or is not connected to one of the elements 1–18 (e1–e18) through the use of two shift registers and associated multiplexing structures. The shift registers are substantially identical, one being for transmit control and another being for receive control. The shift register concept allows the channels C1–C4 to be cycled through the elements e1 to e18. That is, each one of the elements e1–e18 are capable of being connected to each one of the channels C1–C4, and are sequentially shifted so that, at different times, different elements are connected to different channels. Recalling that four MUXes (10) are used, the use of the combination of the four MUXes (10) allows elements e1 to e72 to be controlled so that the entire circular array can be accessed. The first MUX 10-1 controls elements e1–e18, the second 10-2 controls elements e19–e36, the third 10-3 controls elements e37–e52, and the fourth 10-4 controls elements e53–e72. During some transmit and receive cycles, elements will be controlled by two MUX (10) pre-amplifiers, for example, such will be the case for a sub-aperture including elements e18 and e19.

Figure 4:
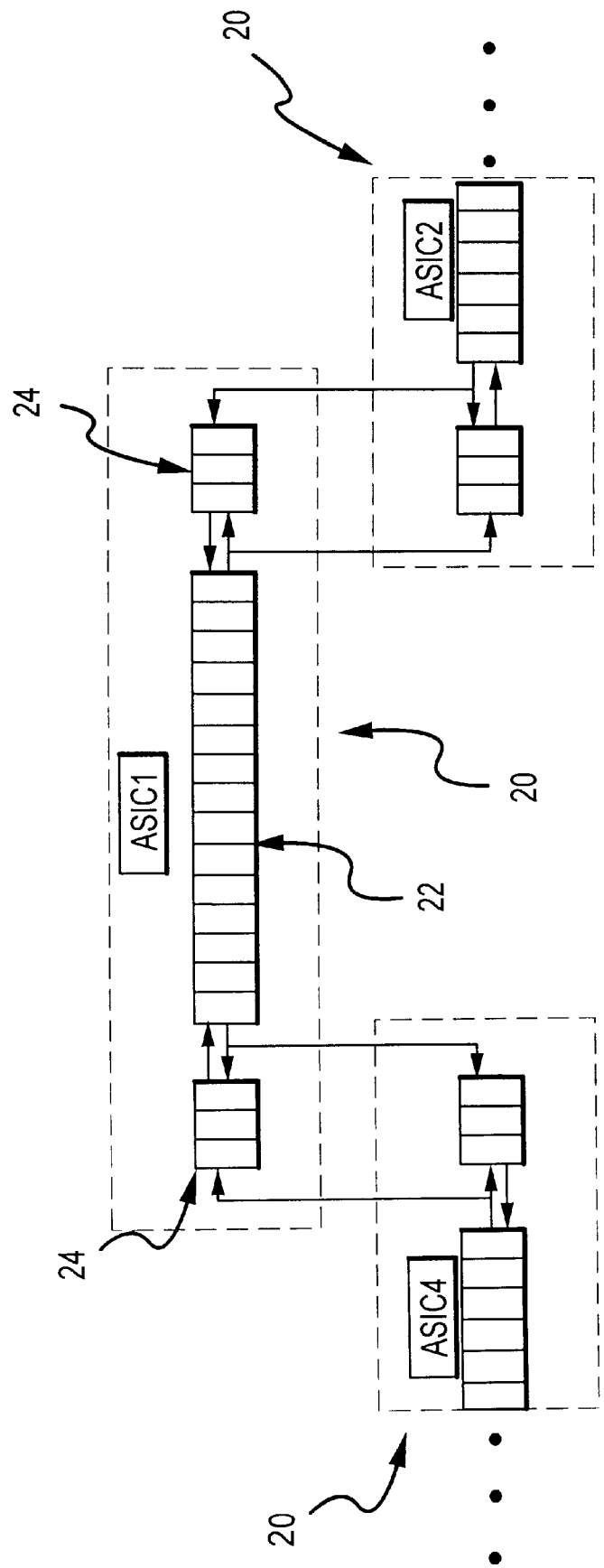
FIG. 4 is a schematic representation of a circular shift register according to an embodiment of the invention.

The shift register concept is explained in connection with a transmit shift register (20) shown representationally in FIG. 4. The shift register (20) is interconnected to an adjacent shift register (20) of another MUX (10), and together the combination circles around the four MUXes (10). Each shift register (20) has twenty-one bits, which can be regarded as a central section of fifteen bits and two end sections of three bits. Each of the two end sections interface with a different adjacent MUX (10). The MUXes are electronically interconnected with one another by the "LOF" and "ROF" pads. The "LOF" of each MUX is connected to the left-most adjacent MUX, and the "ROF" of each MUX (10) is connected to the right-most adjacent MUX adjacent MUX. For example, in the labeling of FIG. 2, MUX 10-1 LOF is connected to MUX 10-4 ROF, and MUX 10-1 ROF is connected to MUX 10-2 LOF. Of course, the directions "left" and "right" are arbitrary and may be reversed.

Image acquisition is initiated by applying a pulse to "reset", which sets exactly one Active High state to one of the shift register (20) bits in one of the MUXes (10). This bit setting corresponds to one sub-aperture. During the next clock cycle, the bit is shifted one position to the right (or left), corresponding to a different adjacent sub-aperture. For example, if elements e1 to e4 are elements comprising the sub-aperture corresponding to the bit position at reset, elements e2 to e5 may be the elements comprising the adjacent sub-aperture. As the selected sub-aperture transcends a boundary between two MUXes, each of the two MUXes will have an active high state in one of the bits of the overlap buffers (24); otherwise only one shift register (20) bit (of the entire group of MUXes) is High.

One of the four MUXes is a master unit, and the other are slave units. The master unit is hardwired by receiving an Active High at the "First" signal, the slaves being hardwired by receiving a Low. In connection with the "reset" input, this ensures that only bit in the entire group of MUXes is High.

The following table summarizes the shifting of the elements through the shift register (20) of one MUX (10). As explained below, physical apertures may be switched by more than one element, so that not every shift register position necessarily corresponds to a physical aperture that is actually used for transmit or receive.

TABLE 2

Shift Register Cycling

| SHIFT REGISTER POSITION | C1 | C2 | C3 | C4 |
|---|---|---|---|---|
| 0 * | nc | nc | nc | nc |
| 1 | nc | nc | nc | e1 |
| 2 | nc | nc | e1 | e2 |
| 3 | nc | e1 | e2 | e3 |
| 4 ** | e1 | e2 | e3 | e4 |
| 5 | e2 | e3 | e4 | e5 |
| 6 ... 17 (repeating pattern) | ... | ... | ... | ... |
| 18 | e15 | e16 | e17 | e18 |
| 19 | e16 | e17 | e18 | nc |
| 20 | e17 | e18 | nc | nc |
| 21 | e18 | nc | nc | nc |
| 0 | nc | nc | nc | nc |

* shift register position at reset if "First" is LOW
** shift register position at reset if "First" is HIGH
nc = not connected.

In shift register positions 1, 2, and 3; and 19, 20, and 21, elements in an adjacent MUX (10) are also active so that a sub-aperture of four elements (e) are selected. The above described shifting sequence shifts the elements (e) to the "right" (from a point of view proximal to the elements (e). The shift register can optionally shift the elements (e) to the left; this option is selected by logic input supplied to the "LRB" pad.

In function, the shift register is could be regarded as an eighteen bit shift register, where each bit corresponds to an element (e). The twenty-one bit implementation, including the central section of fifteen bits and two end sections of three bits each, allows for the seamless control of physical apertures spanning elements controlled by more than one MUX (10), with a minimum of control circuitry.

A receive shift register operates substantially identically to the above described transmit shift register (20).

Summarizing, each MUX (10) includes a twenty-one bit receiving register, with a fifteen bit central section and two three bit overlapping sections. The position of the Active bit within the twenty-one bit register (including all four of the MUXes (10)) selects which group of four (or fewer) elements (e) form a receive sub-aperture.

The MUXes (10) are selected between either a transmit mode or a receive mode by applying a signal to the "RxTxb" pad, a High placing the MUXes (10) in the receive mode and a Low placing the MUXes (10) in a transmit mode.

Figure 7:
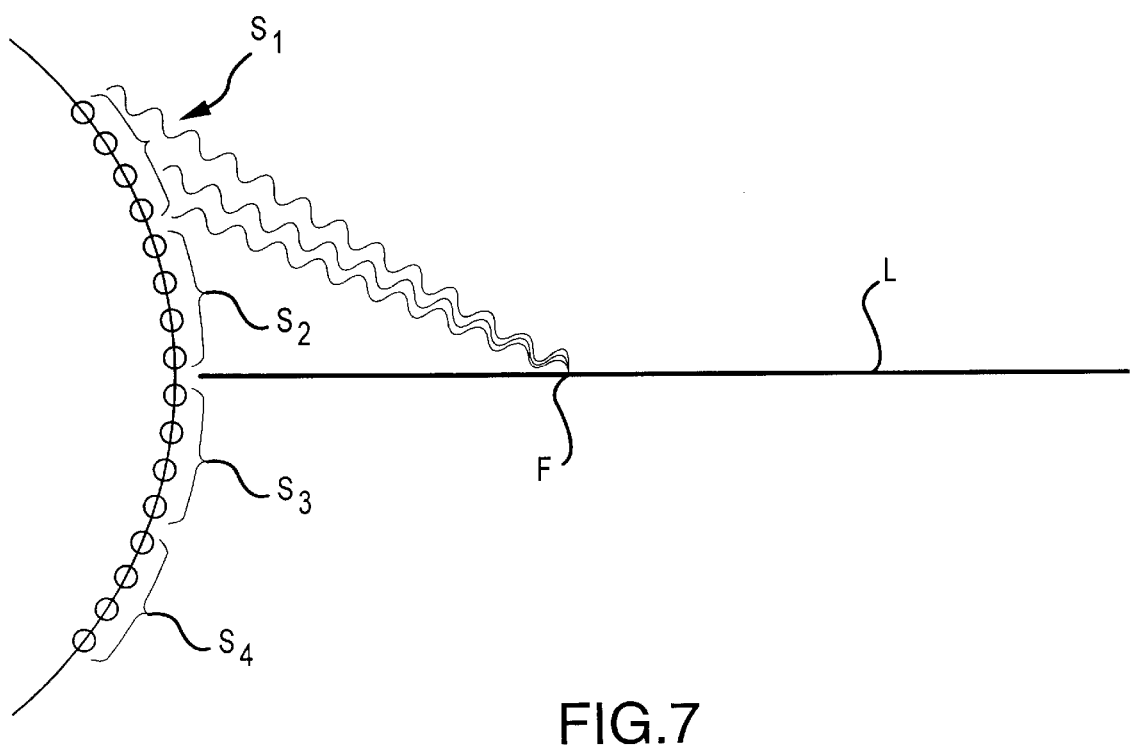
FIG. 7 is a view of a section of an ultrasound array showing various transmit and receive sub-apertures.

Referring to FIG. 7, an example is described to acquire one scanline (designated L) of data taken at a focal point (designated F) along the scanline L. As used herein, a "transmit pulse" is defined as the properly phased pulsing of the four transmit elements (e) in a sub-aperture. The first transmit pulse is from the sub-aperture S1 including elements e1, e2, e3, and e4. The first receive sub-aperture is also sub-aperture S1. The second transmit pulse is again taken from sub-aperture S1. The second receive sub-aperture S2 includes elements e5, e6, e7, and e8. The third receive pulse is again taken 25 from S1, and the third receive sub-aperture S3 includes elements e9, e10, e11, and e12. The fourth transmit pulse is again taken from S1, and the fourth receive aperture S4 includes elements e13, e14, e15, and e16.

The transmit sub-aperture is switched to the sub-aperture S2. Similar to the above-described pattern, the sub-aperture S2 is pulsed four times, each transmit pulse being followed by a receive cycle on one of the sub-aperture S1, S2, S3, and S4. Next, the transmit sub-aperture is switched to the sub-aperture S3. The sub-aperture S3 is pulsed four times, each transmit pulse being followed by a receive cycle on one of S1, S2, S3, and S4. Next, the transmit sub-aperture is switched to the sub-aperture labeled S4.

The above-described transmit and receive cycles provide the data for one scanline of data. In practice, the identical procedure may be produced a number of times and the results averaged. Further, the above combinations of transmit and receive cycles may be repeated with separately phased transmit pulses to acquire one or more additional scanlines and/or one or more focal points, such phasing being well known in the art and not being an integral part of the present invention.

The physical apertures are then stepped over a desired number of elements, and another scanline is taken. The step could be by an individual element, so that a new sub aperture S1 would now include e2, e3, e4, and e5, with the other physical apertures adjusted accordingly. Or, the steps could be another number of elements, such as four, in which case new S1 would now include e5, e6, e7, and e8. In a presently preferred embodiment, the number of steps is one element as described above. In such an embodiment, there are seventy-two physical transmit apertures, each transmit aperture being pulsed and received four times (disregarding repetitions for averaging and for variable phase, if present). However, alternative steps are possible and expressly contemplated as a part of the present invention.

It should be appreciated that the use of the above described sub-apertures allows for cross terms to be included in an ultrasound image while dramatically reducing the number of acquisition cycles that need be made. More particularly, the number of acquisition cycles are reduced by the square of the number of elements forming the sub-aperture. In the above described exemplary case, the sub-aperture has four elements, and the physical aperture has sixteen elements. A total of four sub-apertures are used for transmit, each sub-aperture receiving with four elements. Thus, sixteen transmit/receive cycles are used to create one scanline. Without the use of sub-apertures, sixteen transmit cycles would be necessary, each sub-aperture receiving with sixteen elements, thus requiring 256 cycles per scanline. Most generally, the use of sub-apertures allows the number of acquisition cycles to decrease as the square of the number of elements composing the sub-aperture, as:

Number of Acquisition Cycles Per Aperture=$N^2/M^2$ where N=number of elements per physical aperture and M=number of elements per sub aperture. In the exemplary case, the number of acquisition cycles is reduced by a factor of $4^2$=16.

The MUX pre-amplifier (10) also includes amplifying circuitry to amplify the received signals. The amplification is preferably at least twenty dB, which reduces the distortion effects of both internal and external RF interference and noise as the received signals are transmitted from the array subsystem through cabling to the external system. Impedance matching circuitry translates the impedance of 1500 ohms of the elements (e) to 50 ohms suitable for transmission through the coaxial cables.

Figure 5:
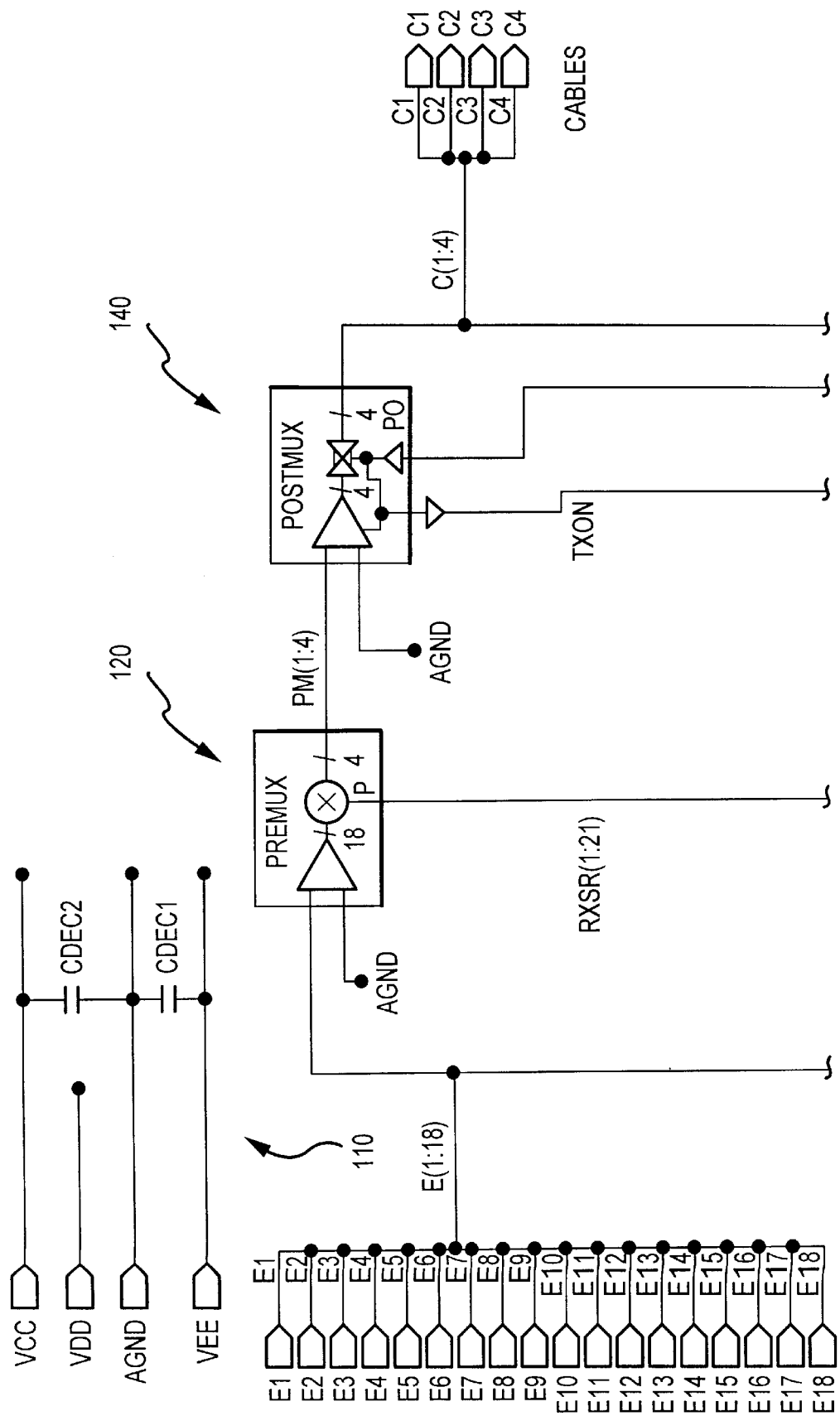
FIG. 5 is a top level circuit schematic of a MUX according to an embodiment of the invention.
Figure 5A:
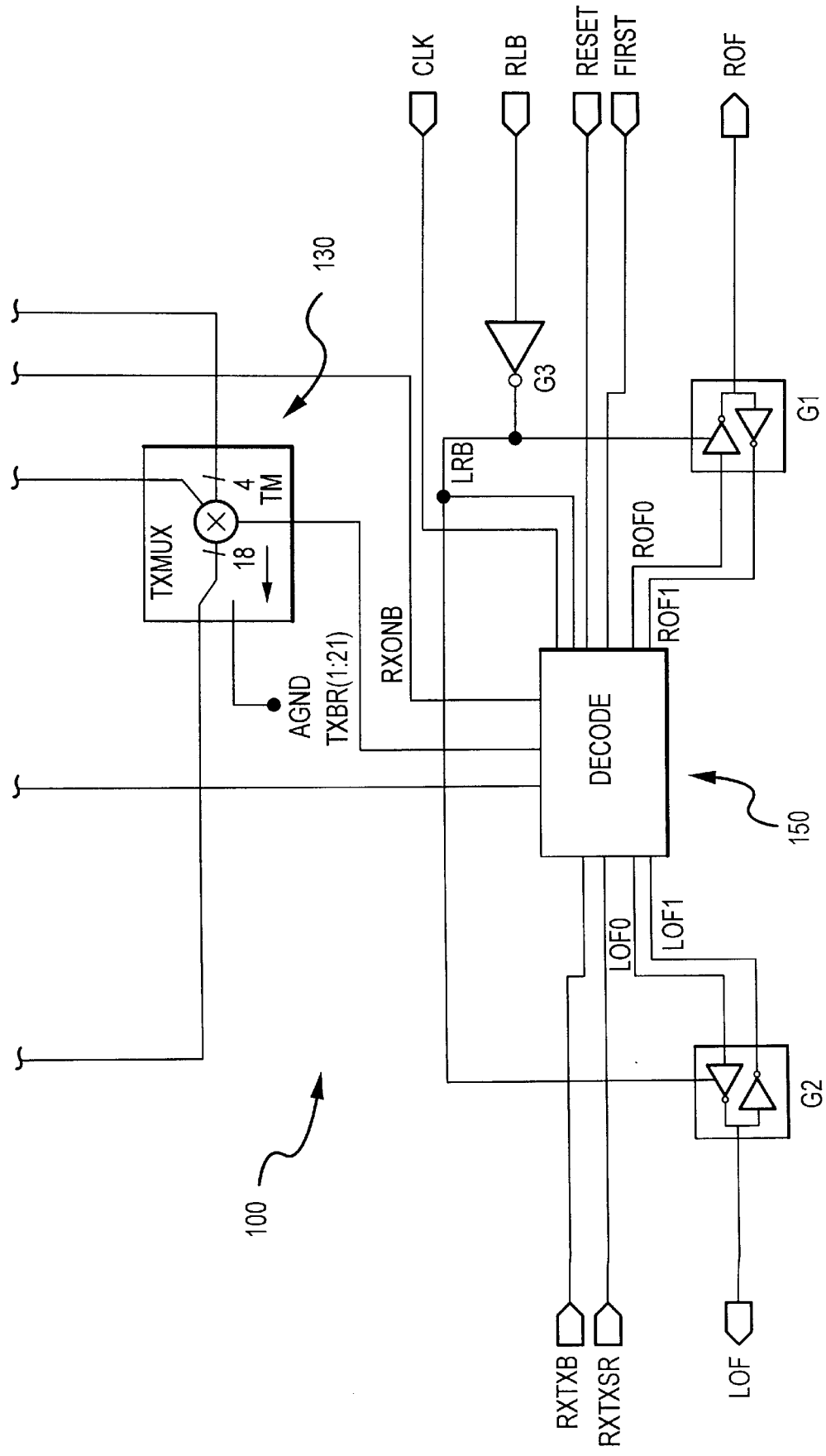

With reference to FIG. 5, a top level circuit schematic diagram of a MUX (10) according to the invention is provided. The power supply and grounding elements are provided at (110). The elements (e) are connected to the first amplifier stage at (120). The transmit multiplexing circuitry is shown at (130). The second amplifier stage is shown at (140). The decoding section is shown schematically at (150), and includes the transmit shift register (20) and receive shift register as described above.

The amplification circuits of each MUX must be capable of low input noise, and extremely fast recovery time as each element is required to be switched between transmit mode and receive mode in about 20 ns. Further, the amplifier must be able to withstand the full transmit signal which can be as high as 8 V peak-to-peak, and also to amplify received signals of around 1 mV or less. The operating performance is realized by splitting the amplifier into two stages, the stages operating between the multiplexing stage. By this it is meant that as the multiplexing transfers the acoustical signal between 18 elements and four coaxial cables, a first amplifier stage operates on the signal between the 18 elements and the multiplexer, and a second amplifier stage operates between the multiplexer and the cables C1–C4.

Figure 6A:
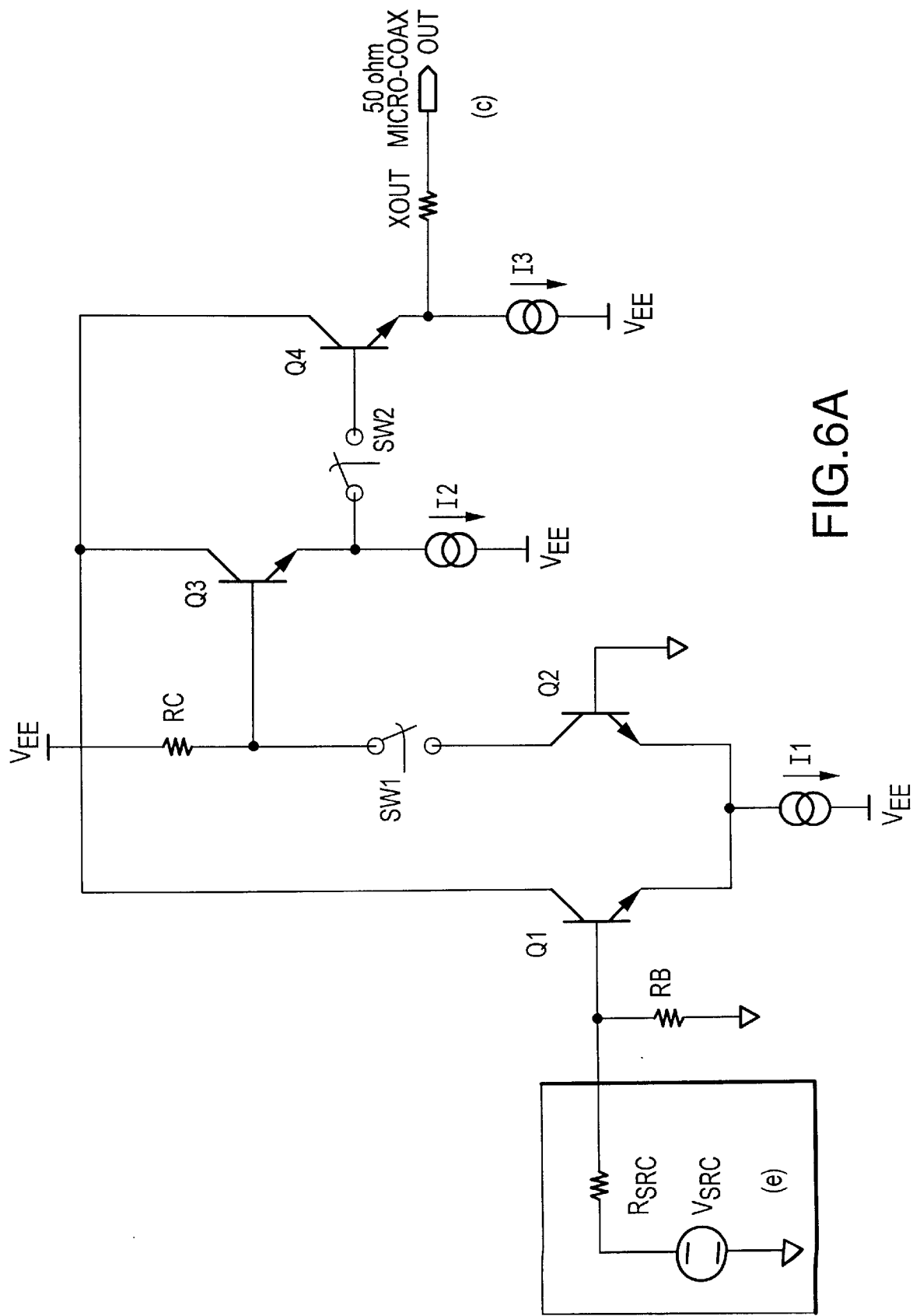
FIG. 6A is a schematic of the receive signal path of the MUX of FIG. 5.

With reference to FIG. 6A, a schematic diagram of the return signal path circuitry between an element (e) and one of the coaxial cables (C1–C4) is shown. The schematic shows necessary operative components. Additional components such as biasing components and buffering components may be added to accomplish desired circuit performance levels.

The ultrasonic element (e) is modeled as a voltage source (Vsrc) in series with an output impedance (Rsrc) on the order of 1.5 kΩ. The circuitry includes an input resistor Rb having a resistance approximately equal to Rsrc to ensure good termination for the ultrasonic element and to permit a dc path into an input amplification stage.

The input amplification stage comprises two transistors (Q1 and Q2) and a current source I1, the base of Q1 seeing the voltage at Rb. A separate input amplification stage is associated with each element (e), so that there a total of eighteen input amplification stages per MUX (40) in a preferred embodiment. The current source I1 can be a switched resistor.

Transistors Q1 and Q2 are selected to be suitably large to provide good low input noise performance, which represents a limiting factor for image fidelity. The output of Q1 is tied high (VDD) to prevent loading effects during a transmission cycle, at which time there is a large signal waveform across the element (e). The output current of Q2 feeds into resistor Rc via a multiplexing switch SW1. The switch SW1 performs the primary multiplexing function from the eighteen elements (e) to the four cable channels (C1–C4). The switch SW1 could be any of a number of electronic switches, and particularly a MOS switch.

A second amplification stage comprises transistors Q3 and Q4 and associated components. A separate second amplification stage is associated with each of the analogue channels (C1–C4), so that there are four second amplification stages per MUX 40. The transistors Q3 and Q4 together with associated current sources I2 and I3 function as a buffer to drive the relatively low impedance load from the relatively high impedance presented by the lower end of resistor Rc. A matching resistor Rout together with the output impedance seen at the emitter of Q4 are set to match the characteristic impedance of the micro-coax cable (about 50 ohms), thereby avoiding reflections and resulting potential instability.

A switch SW2 isolates the receive amplification channel from the cable interface during a transmission cycle, where the relatively large waveforms could unbalance the receive circuits and hence cause an unacceptably large recovery time from transmit to receive.

The small signal gain of the system from the base of Q1 to the emitter of Q4 is given (first order) by the product of half the transconductance of Q1 and the resistance of Rc. The overall voltage gain from the loaded element (e) to the terminated load at the micro-coax cable is 6 dB less, due to the series resistive matching network used. The overall voltage gain is set to about 20 dB as a compromise between noise performance and fidelity of response, due to frequency response limitations and stability.

The current sources I1–I3 are controlled by the decode logic to ensure that only the circuits activated are powered-up, thereby minimizing power consumption and attendant heating. Such control can be accomplished by sensing whether current flows through SW1, and powering the current sources down if not.

Figure 6B:
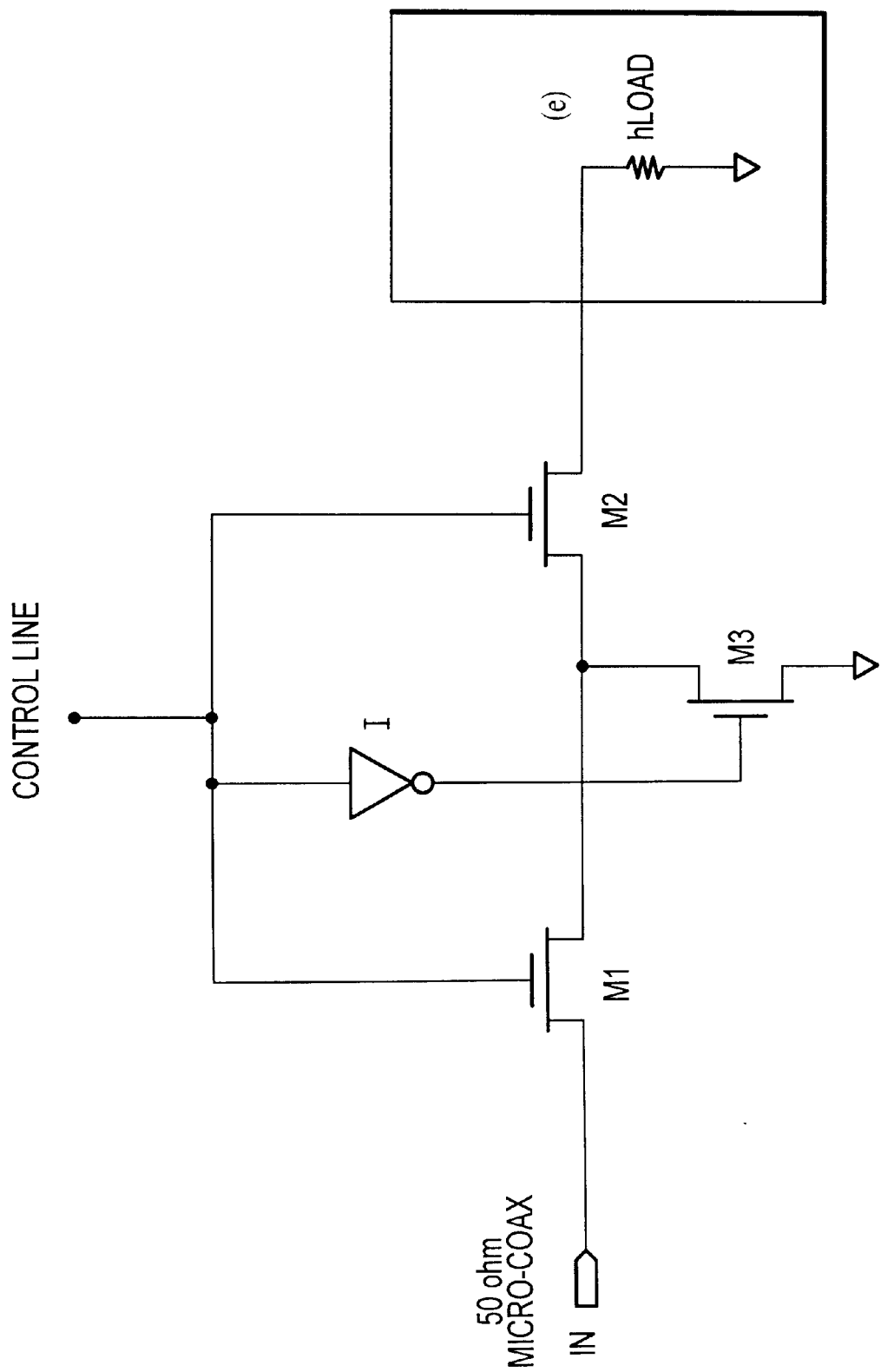
FIG. 6B is a schematic of the transmit signal path of the MUX of FIG. 5.

With reference to FIG. 6B, the transmit signal path between a micro-coax cable of one of the channels (C1–C4) and one of the elements (e) (represented by the resistor RLoad) is shown.

The transmit signal path is designed to transfer the maximum amount of energy to element (e), thereby obtaining the best possible signal-to-noise ration on the receive cycle. The transmit signal path includes a multiplexing switch array comprising two series pass MOS devices (M1 and M2), and one shunt MOS device (M1) driven in anti-phase (accomplished by inverter (I)). The resulting "T" type transmission gate structure allows a low insertion loss to be obtained in the ON mode while obtaining a high isolation impedance in the OFF mode. Each element (e) is potentially associated with each of the four channels (C1–C4), so that seventy-two transmission gates are provided. It may be possible to use fewer transmission gates, if an embodiment is used wherein it is not necessary for each element (e) to be potentially engaged with each channel (C1–C4).

The devices M1 and M2 are preferably each formed of a parallel connection of an n-type device and a p-type device, with gates driven in anti-phase.

It should be understood that the above description is given for the purposes of the illustration and not for limitation, and the present invention is defined by the appended claims and their legal equivalents. In particular, not all of the elements and features described need by employed in a particular embodiment. For example, the described circuitry could be replaced with other circuitry accomplishing essentially the same ends.

What is claimed is:

1. An improved ultrasound mixed signal muitiplexer/preamplifier ASIC device comprising:

means for transmitting a plurality of analogue signals to a transmit sub-aperture of ultrasound elements selected from an ultrasound array, the ultrasound elements transmitting the signals as acoustical pressure;

means for receiving reflected acoustical pressure as analogue signals on a receive sub-aperture of ultrasound elements selected from the ultrasound array;

means for amplifying the analogue signals of said receiving means;

means for transmitting the amplified signals to an ultrasound processing system; and decoding means for selecting the transmit sub-aperture of ultrasound elements from the ultrasound elements of the ultrasound array and for selecting the receive sub-aperture of ultrasound elements from the ultrasound elements of the ultrasound array;

said device being sized for insertion within a lumen of a body;

wherein the decoding means comprise means for sequentially selecting the receive sub-aperture of ultrasound elements from the array ultrasound elements so that more than one receive sub-aperture receives analogue signals from a given transmit sub-aperture.

2. The device of claim 1, wherein the decoding means comprise means for sequentially selecting the transmit sub-aperture of ultrasound elements from the array elements so that more than one transmit sub-aperture transmits acoustical pressure.

3. The device of claim 1, wherein the decoding means comprise a transmit shift register having a number of adjacent positions, each position having a state corresponding to either a digital "high" or a digital "low"; each position corresponding to a different sub-aperture of ultrasound elements; only one of the positions being a digital "high" at any one time so that only one sub-aperture of ultrasound elements is selected at that time.

4. The device of claim 3, wherein the ultrasound elements are arranged in a generally circular configuration, and each shift register position corresponds to a sub-aperture of adjacent ultrasound elements; and adjacent shift register positions correspond to overlapping sub-apertures of ultrasound elements.

5. The device of claim 1, wherein the transmit sub-aperture of ultrasound elements and receive sub-aperture of ultrasound elements include up to four elements each.

6. The device of claim 1, further comprising multiplexing means such that the received signals are multiplexed before being transmitted to the ultrasound processor system, and the amplifying means include a first and a second stage, the first stage amplifying the received signals before multiplexing; and the second stage amplifying the received signals after multiplexing.

7. A method of ultrasound intraluminal imaging, comprising the steps of:

selecting a transmit sub-aperture of ultrasound elements from an array comprising a plurality of subelements;

selecting a receive sub-aperture of ultrasound elements from an array comprising a plurality of subelements;

selecting a receive sub-aperture of ultrasound elements from the array;

transmitting a plurality of analogue signals to the transmit sub-aperture, the ultrasound elements transmitting the signals as acoustical pressure;

receiving reflected acoustical pressure as analogue signals on the receive sub-aperture;

amplifying the reflected signals; transmitting the reflected signals to an ultrasound processing system; said array being sized for insertion within a lumen of a body;

wherein the step, of selecting a receive sub-aperture of ultrasound elements is performed sequentially so that more than one receive sub-aperture receives analogue signals from a given transmit sub-aperture.

8. The method of claim 7, wherein the step of selecting a transmit sub-aperture of ultrasound elements is performed sequentially so that more than one transmit sub-aperture analogue signals from a given receive sub-aperture.

9. The method of claim 8, wherein the step of selecting a transmit sub-aperture includes shifting a bit within a digital shift register.

10. The method of claim 9, wherein the stop of selecting a receive sub-aperture includes shifting a bit within a separate digital shift register than the transmit shift register.

11. The method of claim 10, wherein the steps of selecting transmit sub-apertures and receive sub-apertures include selecting up to four elements for each sub-aperture.

12. The method of claim 11, wherein the step of selecting a receive sub-aperture includes a multiplexing step, and the amplifying includes a first amplification stage before said multiplexing step and a second amplification stage after said multiplexing step.

* * * * *